(12) United States Patent
Happonen et al.

(10) Patent No.: US 6,755,832 B2
(45) Date of Patent: Jun. 29, 2004

(54) BONE PLATE IMPLANT

(75) Inventors: Harri Happonen, Tampere (FI); Timo Pohjonen, Tampere (FI); Tarmo Majava, Tampere (FI)

(73) Assignee: Inion Ltd., Tampere (FI)

( * ) Notice: Subject to any disclaimer, the term of this patent is extended or adjusted under 35 U.S.C. 154(b) by 36 days.

(21) Appl. No.: 10/113,915

(22) Filed: Apr. 1, 2002

(65) Prior Publication Data

US 2002/0165545 A1 Nov. 7, 2002

(30) Foreign Application Priority Data

Apr. 3, 2001 (FI) .............................................. 20010694

(51) Int. Cl.⁷ .............................................. A61B 17/80
(52) U.S. Cl. ...................................................... 606/69
(58) Field of Search ............................... 606/60, 69, 70, 606/71

(56) References Cited

U.S. PATENT DOCUMENTS

| 4,905,679 | A | * | 3/1990 | Morgan ........................ 606/70 |
| 5,984,925 | A | * | 11/1999 | Apgar .......................... 606/69 |
| 6,221,075 | B1 | * | 4/2001 | Tormala et al. ................ 606/77 |
| 6,309,393 | B1 | * | 10/2001 | Tepic et al. .................... 606/69 |

* cited by examiner

Primary Examiner—John J. Wilson
Assistant Examiner—Michael B Priddy
(74) Attorney, Agent, or Firm—Banner & Witcoff, Ltd.

(57) ABSTRACT

A bone plate for supporting bone. At least one shaping area reducing the shaping resistance of the shape of the bone plate and the bending and/or torsional resistance of the body is arranged in the section of the bone plate between fixation holes.

33 Claims, 3 Drawing Sheets

Figure 1:
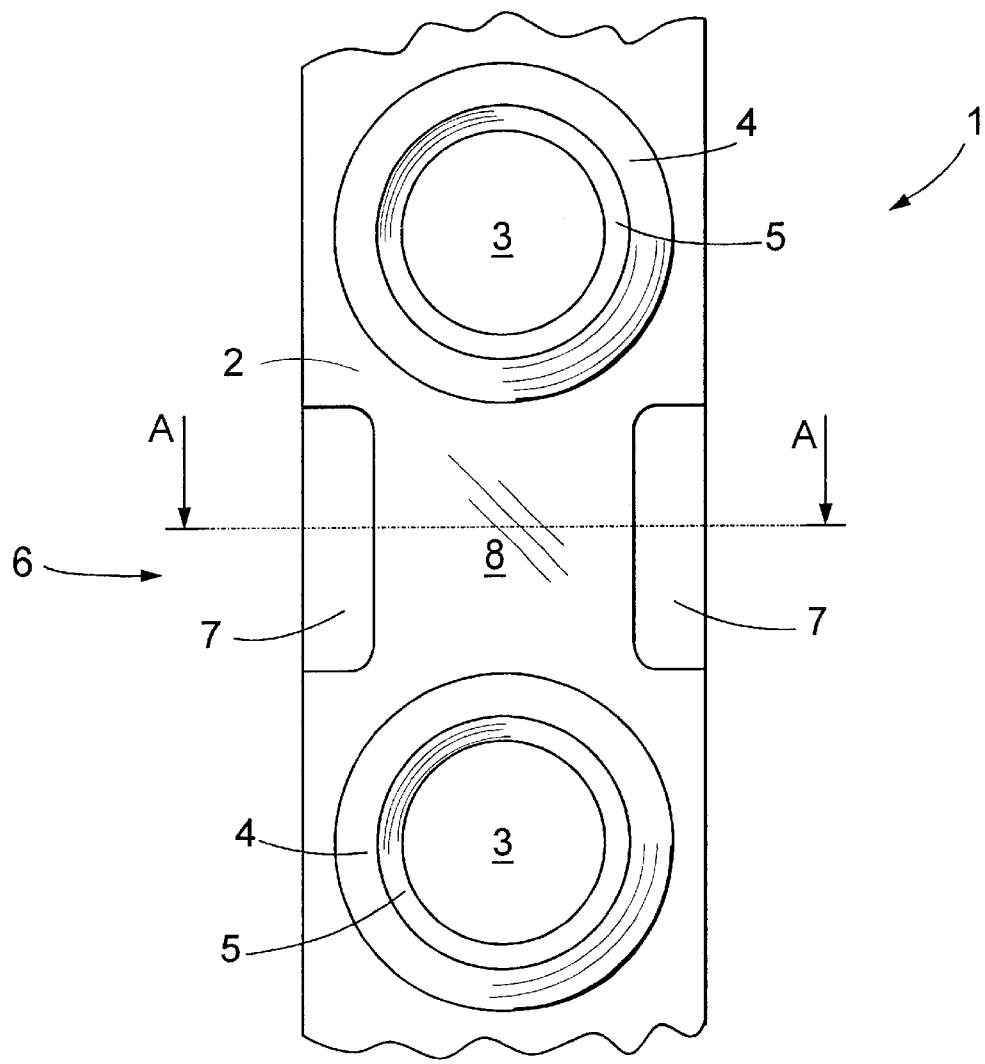

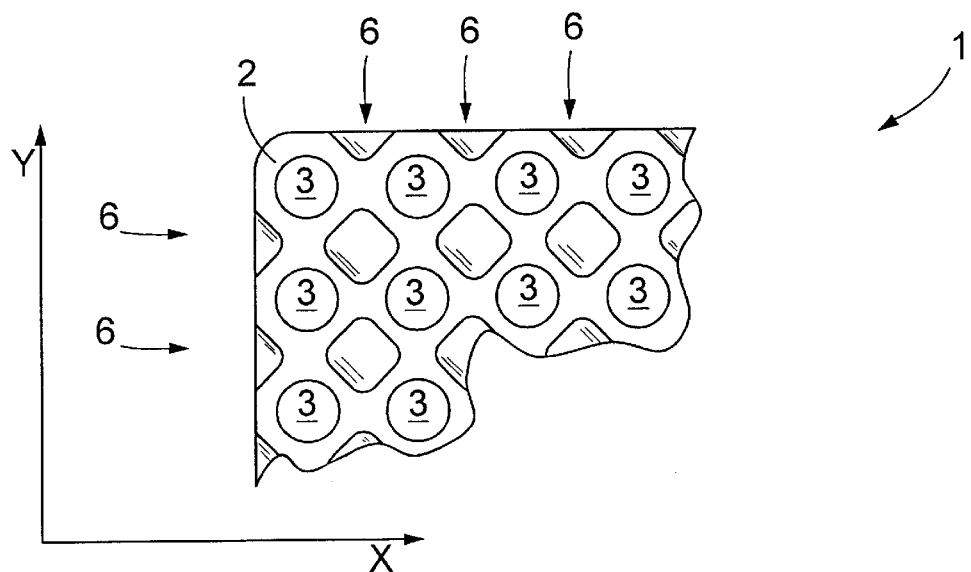
Fig. 6
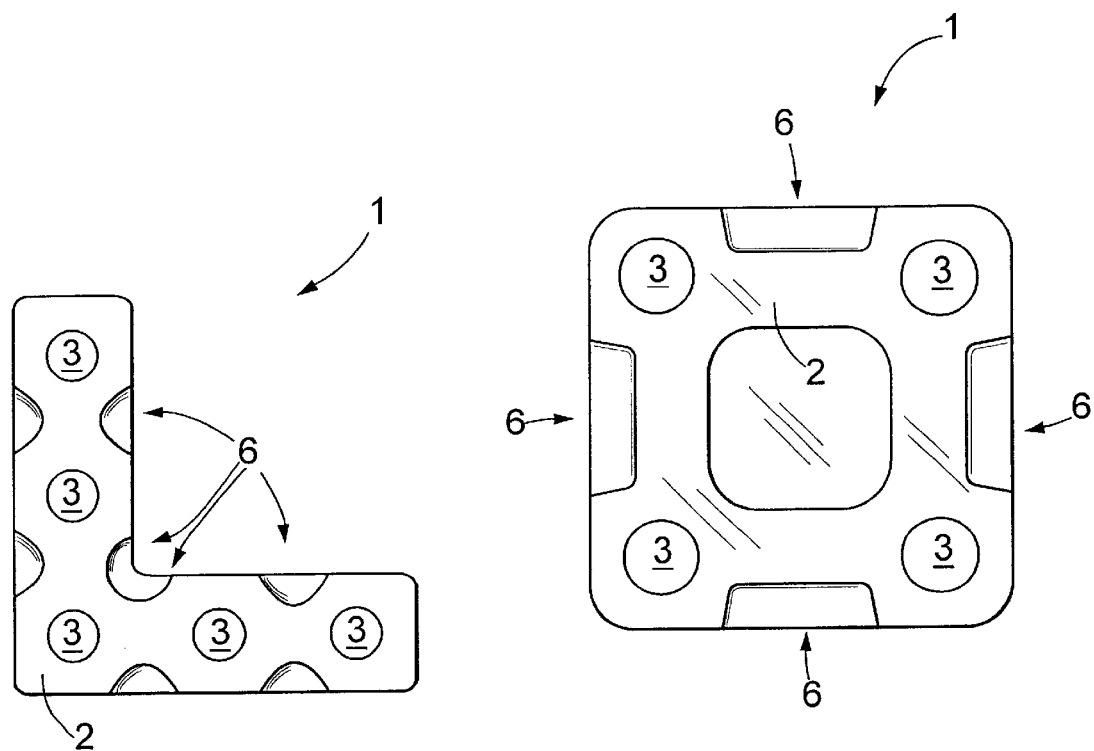
Fig. 7a
Fig. 7b

BONE PLATE IMPLANT

This application claims the benefit of the filing date of Finnish Patent Application No. 20010694, filed Apr. 3, 2001.

The invention relates to a bone plate for supporting bone, which is made of a material absorbing partly or entirely into the system and which bone plate comprises an upper surface, lower surface, and at least two fixation holes that extend through the bone plate from the upper surface to the lower surface, through which fixation holes fixation elements can be arranged for fixing the bone plate to bony tissue.

Implants, i.e. bone plates, supporting a healing bone, used in osteosynthesis and made of materials absorbing into the human system are known. They are often bar-like elongated elements in shape. In the following, said elements are referred to as bone plates.

A bone plate is fixed by fixation elements, such as screws, to the bony tissue to be supported, on both sides of a fractured or cracked bone. The bone plate keeps the bone in a correct position so as to allow the bone to heal in the best possible manner. When the bone plate is made of a material absorbing into the system, it need not be removed from the system, thus avoiding surgery to remove the bone plate after the bone has healed. This is naturally advantageous with respect to patient satisfaction, resource load and costs.

The bone plate is thus elongated in shape and comprises at least two, but in most cases a minimum of four, holes extending through the bone plate, to which fixation elements, such as screws, pins or other corresponding fixation elements known per se, are arranged to fix the bone plate and bone to each other. The basic shape of the cross-section of the bone plate is typically a rectangle. In some applications, the cross-section of the bone plate is higher and often also wider at the fixation holes than in the sections between the fixation holes. This design aims at compensating for the decrease in cross-sectional area of the bone plate caused by the fixation holes that would otherwise reduce the tensile strength of the bone plate. U.S. Pat. No. 3,463,148, for instance, discloses a similar solution, in which the cross-sectional area is substantially constant along the entire length of the bone plate. Tensile strength is a significant variable describing the properties of the bone plate, because the bone plate is in a majority of cases arranged on the convex side of the bone. This side is the tension side of the bone, i.e. on this side, tensile load is exerted to the bone and the bone plate fixed to it.

Appropriate fitting of bone sections to each other requires that the bone plate can be shaped exactly according to the shape of the bone sections being fitted together. The lower surface of the bone plate, which is arranged against the bone to be supported, is in most cases concave, i.e. it curves towards the inside, and in the shape of the cylindrical surface of a longitudinal cylinder of the bone plate, whereby it fits the curved shape of the bone. The sections of the bone plate between the fixation holes should also bend and curl to the shape of the bone sections. Fitting is arduous, because the bending and torsional resistance of the sections of the bone plate between the fixation holes are high and shaping requires a great deal of force—even when using forceps and clamps for fitting. Shaping the bone plate causes a great deal of work during the operation, and consequently, the operation time extends and additional costs accrue. In addition, the fit of the bone plate may remain incomplete, which prevents the use of the bone plate in the application in question, if the bone plate in question is operated to the bone, it may at worst hamper the healing of the bone.

It is an object of the present invention to provide a novel and improved bone plate for use in osteosynthesis and supporting a healing bone.

The bone plate of the invention is characterized in that at least one shaping area reducing the shaping resistance, i.e. bending and/or torsional resistance, of the shape of the bone plate is formed to the section of the bone plate between the fixation holes, the thickness of the edge section of which shaping area is substantially smaller than that of its midsection.

The essential idea of the invention is that in the section of the bone plate between the fixation holes, there are one or more sections reducing the shaping resistance of the bone plate (later shaping area). Further, the essential idea of the invention is that the thickness of the edge section of the cross-section of the shaping area is smaller than the thickness of the section at the centerline of the bone plate. Further, the essential idea of a preferred embodiment of the invention is that the length of the shaping area is substantially equal to the length of the bone plate section between the fixation holes. Further, the essential idea of a second preferred embodiment of the invention is that the maximum width of the shaping area is greater than the basic width of the bone plate.

The invention provides the advantage that the shaping resistance, i.e. bending and/or torsional resistance, of the bone plate is made low, whereby the shaping of the bone plate is essentially easier than in the prior art, without essentially reducing the tensile strength, however. When the shaping area is the longest possible, i.e. essentially as long as the bone plate section between the fixation holes, shaping the bone plate is even easier. By widening the edge sections of the shaping area to make their maximum width greater than the basic width of the bone plate, it is possible to increase the tensile strength of the shaping area without essentially compromising the good shaping properties.

The invention is described in greater detail in the attached drawings, in which

Figure 2:
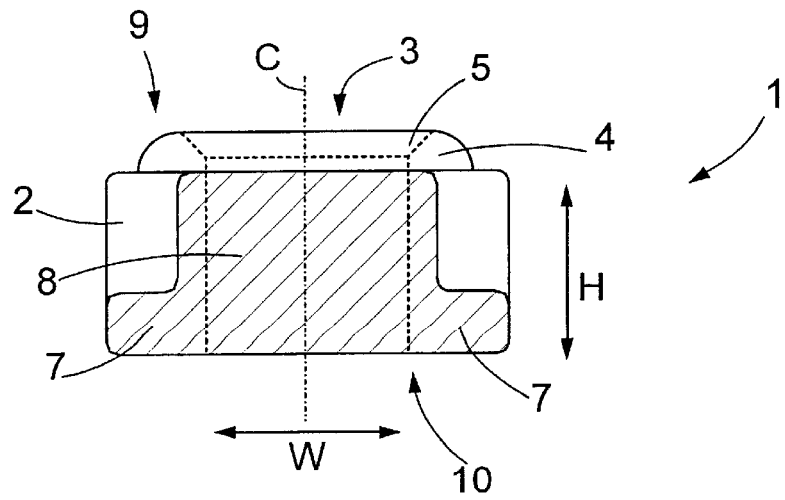
Figure 3:
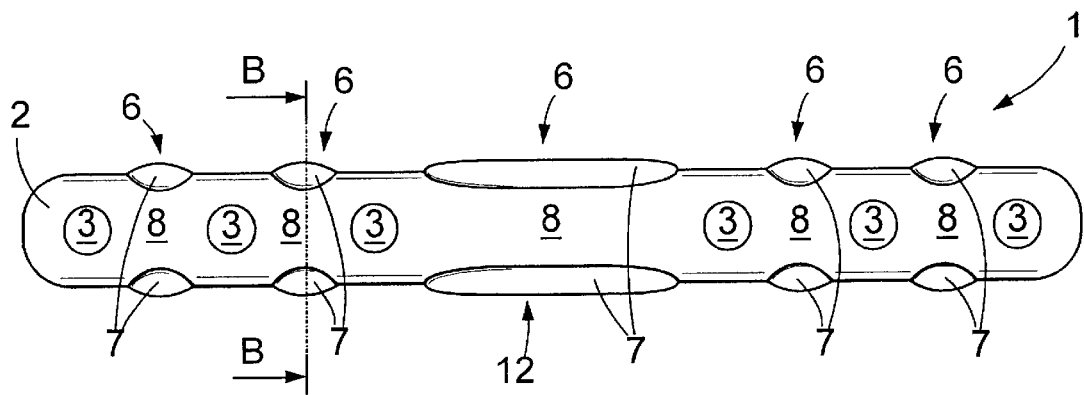
Figure 4:
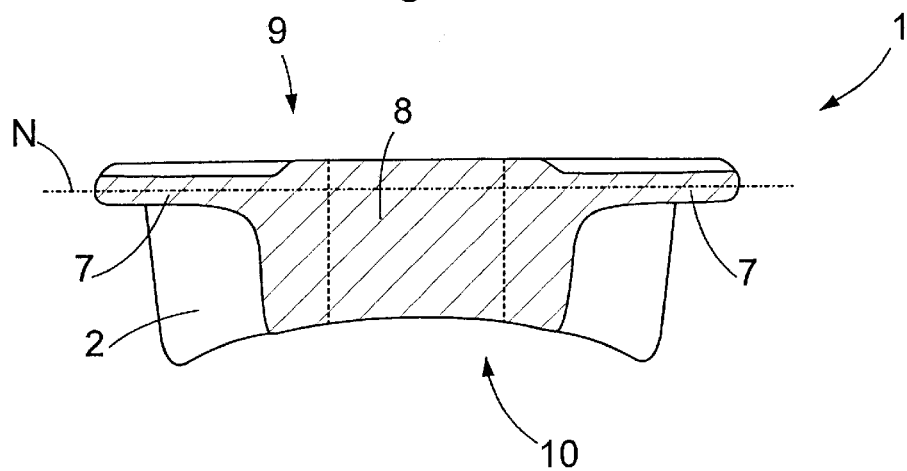
Figure 5:
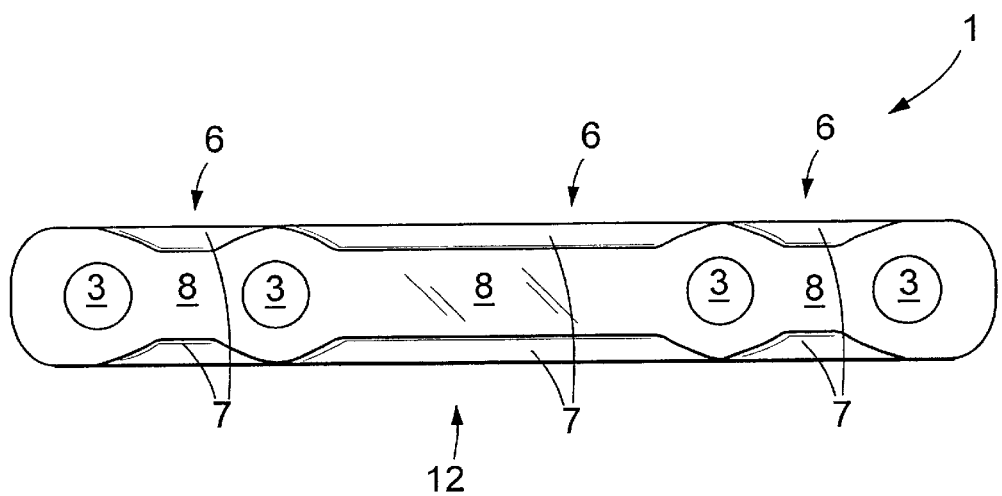

FIG. 1 is a schematic representation of a shaping area of a bone plate of the invention from the direction of the upper surface, FIG. 2 is a schematic cross-sectional view of the bone plate shown in FIG. 1, FIG. 3 is a schematic representation of a second bone plate embodiment of the invention from the direction of the lower surface, FIG. 4 is a schematic cross-sectional view of the bone plate shown in FIG. 3, FIG. 5 is a schematic representation of a third bone plate embodiment of the invention from the direction of the lower surface, FIG. 6 is a schematic representation of a fourth bone plate embodiment of the invention from the direction of the lower surface, and FIGS. 7a and 7b are general schematic representations of some other bone plate embodiments of the invention.

FIG. 1 is a schematic representation of a shaping area of a bone plate of the invention from the direction of the upper surface. The body 2 of the bone plate 1 is made of a biodegradable polymer material absorbing into the human body that is prepared by polymerizing or copolymerizing for instance lactic acid, L-lactide, D-lactide, D,L-lactide, mesolactide, glycolic acid, glycolide or a cyclic ester copolymerized with lactide, or any other corresponding material known per se to a person skilled in the art, which will not be discussed in this context in greater detail. Other suitable biodegradable polymers, copolymers and polymer mixtures are listed in the following publications, for instance:

"*Encyclopedic Handbook of Biomaterials and Bioengineering, Part A,*" Donald, L. Wise, Debra J.

Trantolo, David E. Altobelli, Michael J. Yaszemski, Joseph D. Gresser, Edith R. Schwartz, 1992, by Marcel Dekker, Inc., pages 977 to 1007, "Biodegradable fracture-fixation devices in maxillofacial surgery," R. Suuronen, Int. J. Oral Maxillofac. Surg., 1993, 22: 50 to 57, "Critical Concepts of Absorbable Internal Fixation," William S. Pietrzak, Portland Bone Symposium, Portland, Oreg., Aug. 4 to 7,1999, "High-impact poly(L/D-lactide) for fracture fixation: in vitro degradation and animal pilot study," Jan Tams, Cornelis A. P. Joziasse, Ruud R. M. Bos, Fred R. Rozema, Dirk W. Grijpma and Albert J. Pennings, Biomaterilas 1995, Vol. 16, No. 18, pages 1409 to 1415, "A Review of Material Properties of Biodegradable and Bioresorbable Polymers and Devices for GTR and GBR Applications," Dietmar Hutmacher, Markus B. Hürzeler, Henning Schliephake, The International Journal of Oral & Maxillofacial Implants, Volume 11, Number 5, 1996, pages 667 to 678, and "Orthopaedic Application for PLA-Pga Biodegradable Polymers," Kyriacos A. Athanasiou, Mauli Agrawal, Alan Barber, Stephen S. Burkkhart, The Journal of Arthroscopic and Related Surgery, Vol. 14, No. 7 (October), 1988: 726 to 737.

Further, it is obvious to a person skilled in the art that the material can be a composite that contains two or more materials or monomers, polymer chains, having the essential property of dissolving in the system. A composite can contain bio-glass, bio-ceramics, a pharmaceutical, such as antibiotic or growth factor, or the like.

The part of the bone plate 1 in question comprises two fixation holes 3 made in the body 2 of the bone plate and extending through it. Suitable fixation elements are arranged in the fixation holes 3 to fix the bone plate 1 to bony tissue. The fixation elements in question are typically screws that are screwed to the bony tissue in a manner known per se. The fixation holes 3 are reinforced by a reinforcement 4 that forms a raised collar around the fixation hole 3. The mouth of the fixation hole 3 has a countersink 5, to which the end of the fixation element designed according to the fixation hole 3 may sink in such a manner that it becomes level with the top surface of the reinforcement 4 of the hole. This way, the fixation element does not form a protrusion that would hinder the covering of the bone plate with soft tissue during operation.

The section of the bone plate 1 between the fixation holes 3 has a shaping area 6 that reduces the torsional and/or bending resistance of the bone plate. In the embodiment of the invention, the thickness of the edge sections 7 of the shaping area 6 is substantially smaller than that of the mid-section 8 of the shaping area 6. The design reduces substantially the shaping resistance of the bone plate 1 section between the fixation holes 3 in comparison with a bone plate, in which the basic shape of the body is substantially similar, i.e. of equal thickness, throughout the entire length of the bone plate. Owing to this, the bone plate I is easy to shape in the shape of the bone surface being operated.

In the embodiment of the invention shown in FIG. 1, the shaping area 6 is substantially equal in length to that of the section between the fixation holes 3. This design increases the shaping options provided by the shaping area 6, because the entire section of the body 2 between the fixation holes 3 can easily be shaped.

FIG. 2 is a schematic cross-sectional view of the bone plate shown in FIG. 1. The reference numbering is congruent with the reference numbering of FIG. 1. The cross-sectional area is the area A—A shown in FIG. 1.

The figure shows clearly that the thickness of the edge sections of the shaping area 6 in elevation H of the bone plate is substantially smaller that in the mid-section 8 of the shaping area, i.e. the edge sections are thinner than the mid-section 8 and the body 2 of the bone plate. In width W of the bone plate, the shaping area 6 is equal to the basic width of the bone plate. The basic width of the bone plate refers herein to the width of the bone plate in the cross-sectional plane essentially at the center point of the fixation hole 3 The shaping area 6 is symmetric in relation to the center plane C of the bone plate. The center plane C is an imaginary longitudinal plane of the bone plate that is arranged at the centerline of the bone plate and perpendicular to the lower surface of the bone plate. Owing to the symmetry, the shaping properties of the bone plate 1 are the same in the direction of each side surface 11. The entire bone plate 1 is symmetric in relation to said plane. Such a bone plate 1 is very versatile and suited for different applications. The shape of the bone plate is very advantageous with respect to the tensile strength of the bone plate, because through the edge sections 7, there are straight bearing beams equal to the length of the bone plate.

The invention can also be implemented in such a manner that the shaping area 6 is asymmetric in relation to the center plane C, whereby the shaping properties of the bone plate 1 are different in different directions. The bone plate 1 can even be asymmetric in a different way in relation to the center plane C, for instance curved towards the side. Such bone plates 1 are typically tailored for specific applications.

The fixation holes 3 of the bone plate 1 are arranged concentric in relation to the center plane C of the bone plate 1, but they can also be arranged asymmetric in relation to it.

Around the fixation holes 3, a reinforcement 4 is formed, at which the thickness of the bone plate, i.e. the distance between the lower surface 10 and the upper surface 9 perpendicular H to the lower surface 10, is at its maximum. The reinforcement 4 reduces the tensile stress at the fixation hole 3 by compensating for the decrease in the cross-sectional area of the bone plate 1 caused by the fixation hole 3. The reinforcement 4 also increases the strength of the hole area during the pressure caused by the fixation element arranged in the hole.

The design of the shaping area 6 reduces shaping resistance especially when the bone plate 1 is bent in such a manner that the bending center point is on the lower surface 10 side. The shaping area 6 also reduces the shaping resistance when the bone plate is bent to the opposite direction, in other words, when the bending center point is on the upper surface 9 side, and also when the bone plate 1 is bent to either side, or when the bone plate 1 is twisted around its longitudinal axis.

The shaping area 6 is preferably made during one of the manufacturing stages of the bone plate 1: its shape can be produced for instance during the injection-molding or compression stage directly in the mold of the bone plate 1, or it is worked mechanically by machining to the bone plate blank.

FIG. 3 is a schematic representation of a second bone plate embodiment of the invention from the direction of the lower surface. The bone plate 1 has a total of six fixation holes 3 that are grouped in two three-hole groups with an intermediate part 12 on both sides. The bone plate 1 is fixed to the bone in such a manner that the fracture is at the intermediate part 12 and the bone plate is fixed by means of one fixation hole group to one side of the fracture and by means of the other fixation hole group to the opposite side of the fracture.

The bone plate 1 comprises shaping areas 6 in each section between fixation holes 3 and in the intermediate part 12. This is not absolutely necessary, and one of said sections can be ordinary, without the shaping area 6. The maximum width of the shaping area 6 is substantially greater than the basic width of the bone plate. This compensates for the decrease in cross-sectional area of the bone plate 1 caused by the thinness of the edge sections of the shaping area and reduces significantly stress concentrations in the body 2 and the reduction of tensile strength caused thereby.

FIG. 4 is a schematic cross-sectional view of the shaping area 6 of the bone plate of FIG. 3 on the cross-sectional plane B—B shown in FIG. 3. The thickness of the edge sections 7 of the shaping area 6 has been reduced on both the upper and lower surface 9, 10 side. Reducing the thickness on any surface side in the shaping area 6 refers herein to making the shape of the surface in the shaping area 6 such that it is substantially closer to the surface on the opposing side of the body 2 than in the section of the body 2 outside the shaping area 6.

The edge sections 7 are preferably arranged on the neutral plane N of the bone plate. The neutral plane N is the plane where the tension of the bent bone plate is zero. When the edge sections 7 are arranged in this manner, shaping resistance caused by the edge sections 7 is at minimum while the tensile strength is still good.

FIG. 5 is a schematic representation of a third bone plate embodiment of the invention from the direction of the lower surface. The shaping area 6 is extremely long: it extends from one center point of consecutive fixation holes 3 to another. Owing to the long shaping area 6, the bone plate 1 can be bent or twisted to very large angles, which enables the use of the bone plate in different operations.

FIG. 6 is a schematic representation of a section of a fourth bone plate embodiment of the invention from the direction of the upper surface. The bone plate 1 is sheet-like and has several fixation holes 3 arranged in rows on both the X-axis and the Y-axis. The sections of the bone plate 1 between the fixation holes 3 have shaping areas 6 that are also arranged in rows on both the X-axis and the Y-axis. The shaping areas 6 are arranged in relation to the fixation holes 3 in such a manner that there are several shaping areas 6 side by side in the cross-section of the bone plate 1 in both X and Y direction and the shaping areas 6 are thinner in their edge sections than in their center section. In other words, the body 2 of the bone plate has in the X and Y directions a thick network or lattice structure having fixation holes 3 at the intersections and thin shaping area 6 edges in the sections between. Naturally, the fixation holes 3 can be placed in some other known manner: they can be arranged diagonally in relation to the edge of the bone plate 1, or in a subgroup of a certain shape, which subgroups are then arranged in a suitable order to the bone plate 1, or in any corresponding manner.

FIGS. 7a and 7b show schematic representations of some other basic shapes of the bone plate of the invention. The bone plate 1 of the invention can be an elongated bar, or an L bone plate as shown in FIG. 7a or its mirror image, a square bone plate as shown in FIG. 7b, a T, X, or Y bone plate, a bone plate having a certain curved shape, or a bone plate of any other shape known per se.

The drawings and the related description are only intended to illustrate the idea of the invention. The invention may vary in detail within the scope of the claims. Thus, the number of fixation holes 3 can be other than that shown in the figures. The bone plate of the invention can, in principle, be as long or wide as required. By arranging the cross-sectional areas and shape factors of the bone plate 1 along its entire length, it is possible to standardize the tensile stress in the bone plate 1 to be substantially equal along the entire length of the bone plate 1.

What is claimed is:

1. A bone plate for supporting bone, which is made of a material absorbing partly or entirely into the system and which bone plate comprises an upper surface, lower surface, and at least two fixation holes that extend through the bone plate from the upper surface to the lower surface, wherein fixation elements can be arranged through the fixation holes for fixing the bone plate to bony tissue, wherein at least one shaping area reducing the shaping resistance of the shape of the bone plate is formed to the section of the bone plate between the fixation holes, the thickness of an edge section of which shaping area is substantially smaller than that of its mid-section (8), wherein the thickness of the edge section of the shaping area is reduced on the side of the upper surface.

2. A bone plate as claimed in claim 1, wherein fixation holes and shaping areas are arranged to the bone plate in a two-dimensional order.

3. A bone plate as claimed in claim 1, wherein the thickness of the edge section of the shaping area is further reduced on the side of the lower surface.

4. A bone plate as claimed in claim 1, wherein a cross-section of the shaping area is substantially symmetric in relation to the center plane.

5. A bone plate as claimed in claim 1, wherein the shaping area is substantially equal in width to the basic width of the bone plate.

6. A bone plate as claimed in claim 1, wherein a smallest cross-sectional area of the shaping area is substantially equal to the area of a cross-sectional plane arranged at the center point between the fixation holes.

7. A bone plate as claimed in claim 1, wherein thickness of the bone plate is greatest at the fixation holes.

8. A bone plate as claimed in claim 1, wherein edge sections of the shaping area are arranged to be substantially on the neutral plane of the bone plate.

9. A bone plate as claimed in claim 1, wherein a section of the shaping area that reduces the shaping resistance is substantially equal in length to the length of the section of the bone plate between the fixation holes.

10. A bone plate as claimed in claim 1, wherein the greatest width of the shaping area is greater than the basic width of the bone plate.

11. A bone plate for supporting bone, which is made of a material absorbing partly or entirely into the system and which bone plate comprises an upper surface, lower surface, and at least two fixation holes that extend through the bone from th upper surface to the lower surface, wherein fixation elements can be arranged through the fixation holes for fixing the bone plate to bony tissue, wherein at least one shaping area reducing the shaping resistance of the shape of the bone plate is formed to the section of the bone plate between the fixation holes, the thickness of an edge section of which shaping area is substantially smaller than that of its mid-section (8), wherein edge sections of the shaping area are arranged to be substantially on the neutral plane of the bone plate.

12. A bone plate as claimed in claim 11, wherein fixation holes and shaping areas are arranged to the bone plate in a two-dimensional order.

13. A bone plate as claimed in claim 11, wherein the thickness of the edge section of the shaping area is reduced on the side of the lower surface.

14. A bone plate as claimed in claim 11, wherein a cross-section of the shaping area is substantially symmetric in relation to the center plane.

15. A bone plate as claimed in claim 11, wherein the shaping area is substantially equal in width to the basic width of the bone plate.

16. A bone plate as claimed in claim 11, wherein a smallest cross-sectional area of the shaping area is substantially equal to the area of a cross-sectional plane arranged at the center point between the fixation holes.

17. A bone plate as claimed in claim 11, wherein thickness of the bone plate is greatest at the fixation holes.

18. A bone plate as claimed in claim 11, wherein the thickness of the edge section of the shaping area is reduced on the side of the upper surface.

19. A bone plate for supporting bone, which is made of a material absorbing partly or entirely into the system and which bone plate comprises an upper surface, lower surface, and at least two fixation holes that extend through the bone plate from the upper surface to the lower surface, wherein fixation elements can be arranged through the fixation holes for fixing the bone plate to bony tissue, wherein at least one shaping area reducing the shaping resistance of the shape of the bone plate is formed to the section of the bone plate between the fixation holes, the thickness of an edge section of which shaping area is substantially smaller than that of its mid-section (8), wherein a section of the shaping area that reduces the shaping resistance is substantially equal in length to the length of the section of the bone plate between the fixation holes.

20. A bone plate as claimed in claim 19, wherein fixation holes and shaping areas are arranged to the bone plate in a two-dimensional order.

21. A bone plate as claimed in claim 19, wherein the thickness of the edge section of the shaping area is reduced on the side of the lower surface.

22. A bone plate as claimed in claim 19, wherein a cross-section of the shaping area is substantially symmetric in relation to the center plane.

23. A bone plate as claimed in claim 19, wherein the shaping area is substantially equal in width to the basic width of the bone plate.

24. A bone plate as claimed in claim 19, wherein a smallest cross-sectional area of the shaping area is substantially equal to the area of a cross-sectional plane arranged at the center point between the fixation holes.

25. A bone plate as claimed in claim 19, wherein thickness of the bone plate is greatest at the fixation holes.

26. A bone plate as claimed in claim 19, wherein the thickness of the edge section of the shaping area is reduced on the side of the upper surface.

27. A bone plate for supporting bone, which is made of a material absorbing partly or entirely into the system and which bone plate comprises an upper surface, lower surface, and at least two fixation holes that through the bone plate from the upper surface to the lower surface, wherein fixation elements can be arranged through the fixation holes for fixing the bone plate to bony tissue, wherein at least one shaping area reducing the shaping resistance of the shape of the bone plate is formed to the section of the bone plate between the fixation holes, the thickness of an edge section of which shaping area is substantially smaller than that of its mid-section (8), wherein the greatest width of the shaping area is greater than the basic width of the bone plate.

28. A bone plate as claimed in claim 27, wherein fixation holes and shaping areas are arranged to the bone plate in a two-dimensional order.

29. A bone plate as claimed in claim 27, wherein the thickness of the edge section of the shaping area is reduced on the side of the lower surface.

30. A bone plate as claimed in claim 27, wherein a cross-section of the shaping area is substantially symmetric in relation to the center plane.

31. A bone plate as claimed in claim 27, wherein a smallest cross-sectional area of the shaping area is substantially equal to the area of a cross-sectional plane arranged at the center point between the fixation holes.

32. A bone plate as claimed in claim 27, wherein thickness of the bone plate is greatest at the fixation holes.

33. A bone plate as claimed in claim 27, wherein the thickness of the edge section of the shaping area is reduced on the side of the upper surface.

* * * * *